United States Patent [19]

Roscher et al.

[11] 4,010,198

[45] Mar. 1, 1977

[54] PROCESS FOR THE PREPARATION OF ALLYL ACETATE

[75] Inventors: Günter Roscher, Kelkheim, Taunus; Heinz Schmitz, Frankfurt am Main, both of Germany

[73] Assignee: Hoechst Aktiengesellschaft, Frankfurt am Main, Germany

[22] Filed: Oct. 3, 1974

[21] Appl. No.: 511,677

Related U.S. Application Data

[63] Continuation of Ser. No. 167,182, July 29, 1971, abandoned.

[30] Foreign Application Priority Data

July 31, 1970  Germany ................................ 2038120

[52] U.S. Cl. .................................................. 260/497 A
[51] Int. Cl.$^2$ ............................................. C07C 67/04
[58] Field of Search ................................ 260/497 A

[56] References Cited

UNITED STATES PATENTS

| | | | |
|---|---|---|---|
| 3,275,680 | 9/1966 | Holzrichter | 260/497 A |
| 3,300,528 | 1/1967 | Wakasa | 260/497 A |
| 3,600,429 | 8/1971 | Kronig | 260/497 A |
| 3,855,280 | 12/1974 | Severs | 260/497 A |
| 3,925,452 | 12/1975 | Swodenk | 260/497 A |

OTHER PUBLICATIONS

B330,536, Jan. 1, 1975, Swodenk, 260/497 A.

*Primary Examiner*—Anton H. Sutto
*Assistant Examiner*—Michael Shippen
*Attorney, Agent, or Firm*—Curtis, Morris & Safford

[57] ABSTRACT

Process for the preparation of allyl acetate from acetic acid, propylene and oxygen in the gaseous phase in the presence of catalysts containing noble metals, using technical crude olefins containing less than 50 per cent by volume of propylene apart from propane.

3 Claims, 1 Drawing Figure

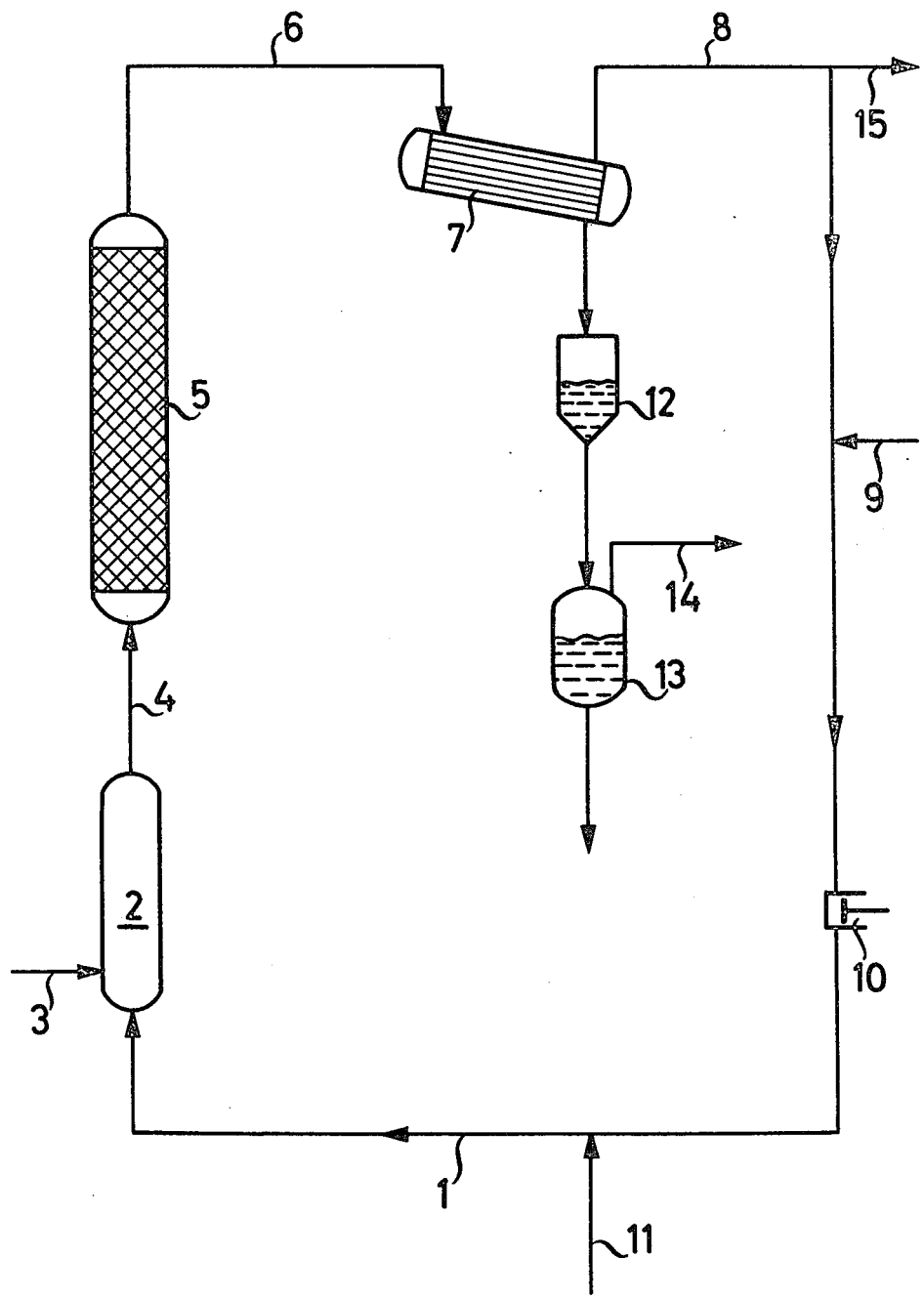

PROCESS FOR THE PREPARATION OF ALLYL ACETATE

This is a continuation of application Ser. No. 167,182, filed July 29, 1971, now abandoned.

The preparation of alkenyl esters by reaction of olefins with carboxylic acids and oxygen in the presence of noble metal containing catalysts in the gaseous phase is known. Thus, when using ethylene, vinyl acetate is obtained, when using propylene, allyl acetate is prepared. Generally, the reaction is carried out at temperatures of from 150° to 250° C and under pressures of from 1 to 10 atmospheres. As catalysts, noble metal salts or noble metals of the 8th sub-group of the periodic system are used, for example palladium, platinum, ruthenium, rhodium, iridium, containing specific additives such as cadmium, gold, bismuth, copper or manganese. The catalysts furthermore contain alkali metal or alkaline earth metal salts. As carrier material, for example silicic acid, aluminium oxide or aluminium silicate may be used. A great number of various catalysts is known.

When applying these processes on a technical scale, generally the carboxylic acid together with the olefin and the oxygen is passed over the catalyst under the aforementioned reaction conditions. The portions which have not reacted in the reaction zone are recycled. The question whether also technical crude olefins may be used in these processes for the preparation of alkenyl esters has been examined for the case of the preparation of vinyl acetate from ethylene, acetic acid and oxygen. It proved however that the ethylene used for the vinyl acetate reaction must not contain any by-products, unless in traces. The ethylene to be used for this purpose corresponds to the ethylene used for polymerization purposes with regard to its quality. In the case where, for example, ethylene containing a small percentage of ethane is used, the vinyl acetate reaction is unprofitable because of ethane concentration in the circuit which results in a considerable decrease of the catalyst efficiency.

Moreover, at decreasing ethylene concentration in the reaction gas, the amount of ethylene which is burned to $CO_2$ and to water in a side reaction increases considerably, thus resulting in a decrease of the ethylene yield.

A process has now been found for the preparation of allyl acetate from acetic acid, propylene and oxygen in the presence of $CO_2$ in the gaseous phase using catalysts containing noble metals or noble metal salts, wherein the concentration of propylene in the reaction gas is below 50% by volume, preferably below 30% by volume, and the reaction is carried out in the presence of a 0.2 to 5.0 fold, preferably 0.5 to 2.0 fold amount of propane, calculated on the amount of propylene. Surprisingly, the process of the invention proceeds smoothly at temperatures of from 140° to 250° C and under a pressure of from 1 to 10 atmospheres without the aforementioned drawbacks occurring while reacting ethylene to vinyl acetate.

Furthermore, the following surprising facts have been revealed: The allyl acetate reaction can be carried out without a substantial decrease of the allyl acetate space-time-yield and the propylene yield at a propylene concentration in the reaction gas at which, for example, the vinyl acetate reaction is nearly stopping when the ethylene content corresponds to that of the propylene. The propylene yield does not decrease as does the ethylene yield while preparing vinyl acetate, and a propane content in the reaction gas which exceeds the propylene concentration has nearly no influence on the allyl acetate reaction, while, in the vinyl acetate process, exceedingly high ethane amounts result in undesirable side reactions.

The possibility of carrying out the allyl acetate reaction at low concentrations of proylene in the presence of large amounts of propane or other hydrocarbons, for example butane or isobutane, increases the profitability of the process.

Instead of expensive propylene of high purity degree, as it is used for example for the polymerization, substantially cheaper impure propylene may be used which may contain for example 10 and more per cent of propane. On account of the possibly high propane content in the reaction gas together with the exhaust gas necessary for the elimination of the propane the propylene amounts lost are only small ones. Furthermore, there is the possibility of eliminating together with the propane, the $CO_2$ formed during the reaction as by-product by the burning of propylene, so that the expenses for an additional absorption washing in order to eliminate the $CO_2$ can be saved. The propane and the $CO_2$ can be eliminated from the reaction system in a simple manner by means of the gaseous portions dissolved in the liquid products during the condensation, which portions escape when the pressure of the condensates is released.

The following examples prove that the allyl acetate reaction results in a still economically interesting allyl acetate space-time-yield when carried out even at very low propylene concentrations in the reaction gas in the presence of a propane amount exceeding the corresponding propylene amount.

The process of the invention is advantageously carried out according to the scheme of the accompanying drawing. The circulating gas flow 1 is led through acetic acid evaporator 2, in which acetic acid 3 is vaporized. The gas mixture loaded with acetic acid passes on to reactor 5 via conduit 4. The reactor has a length of 5.60 m and an inside diameter of 32 mm. The temperature is controlled by an outer jacket containing boiling water the temperature of which is regulated by an automatic maintenance of pressure. The gas leaving the reactor is led to condenser 7 via conduit 6. In the condenser the condensable portions, substantially allyl acetate, non-reacted acetic acid and water, are liquified. The remaining gas mixture is recycled for reaction via conduit 8 and compressor 10. Fresh propylene is added via conduit 9 by means of a pressure maintenance valve at the suction face of the compressor. Via conduit 11, fresh oxygen is added to the circulating gas. The liquid product leaving condenser 7 is collected in receiver 12 having an automatic control of the content. The pressure of the condensates is released in vessel 13. The gas portions dissolved under pressure and freed by the release are allowed to escape via conduit 14. Exhaust gas can be drawn off the gas circuit via conduit 15.

The following Examples illustrate the invention; the percentages being by weight unless otherwise stated.

EXAMPLE 1

The reactor is charged with 4.4 liters of a catalyst containing 1.4% of palladium acetate and 3% of potassium acetate on a silicic acid carrier (balls of a diameter of 5–6 mm). The percentages indicated are calculated on the metal amount.

At a pressure before the reactor of 6.0 atm/g and a catalyst temperature of 193° C, 9.4 m³N per hour of a gas mixture is passed over the catalyst, which gas mixture contains
  67% by volume of propylene
  15% by volume of acetic acid
  8% by volume of oxygen
  10% by volume of carbon dioxide.

The concentration of carbon dioxide in the circulating gas is adjusted by means of the exhaust gas.

In condensation vessel 13, 5 kg of liquid product per hour are obtained which contain 50% of acetic acid, 9.2% of water, 40% of allyl acetate and about 0.8% of by-products. The allyl acetate space-time-yield is 455 g per liter per hour.

In the reaction, 1 mol of water is formed per mol of allyl acetate. The water amount exceeding this stoichiometric ratio is formed by total oxidation of propylene, hereinafter called propylene loss. 3 Mols of water (and 3 mols of $CO_2$) are formed per mol of propylene. On the basis of the allyl-acetate/water ratio in the crude condensate, a propylene loss (calculated on allyl acetate plus loss) of 8.4% is determined.

EXAMPLE 2

The reaction conditions are analogous to Example 1, but the exhaust gas of the gas circuit is adjusted in such a manner as to obtain a $CO_2$ concentration in the gas entering the reactor of 30% by volume, which corresponds to a propylene concentration of 47% by volume. 4.9 kg of crude condensate are obtained per hour. The concentration of allyl acetate is 38.5%, that of the water 9.1%, the amount of by-products is 0.9%. The allyl acetate space-time-yield is 430 g per liter per hour, the propylene loss 9%.

EXAMPLE 3

The reaction conditions are analogous to Example 1, but the exhaust gas is taken off, leaving only the amounts necessary for the analysis apparatuses. The $CO_2$ concentration in the gas entering the reactor is 84% by volume, which corresponds to a propylene concentration of 29% by volume. 4.7 kg of crude condensate per hour are obtained. The allyl acetate concentration is 34.5%, that of the water 7.9%, which corresponds to an allyl acetate space-time-yield of 370 g per liter per hour and a propylene loss of 9.1%. The concentration of other by-products is 0.7%.

EXAMPLE 4

The reaction conditions are analogous to Example 3, i.e. the exhaust gas is taken off, leaving only the amounts necessary for the analysis apparatuses. From a cylinder containing $CO_2$ such an amount of $CO_2$ is added to the circulating gas as to obtain a $CO_2$ concentration in the gas entering the reactor of 65% by volume and a propylene concentration of 12% by volume. The amount of crude condensate obtained per hour is 4.6 kg, the allyl acetate concentration is 32%, that of the by-products 0.7%. The concentration of water is 7.3%, corresponding to an allyl acetate space-time-yield of 325 g per liter per hour and a propylene loss of 7.9%.

EXAMPLE 5

The reaction conditions are analogous to Example 1, but the exhaust gas amount is adjusted in such a manner as to obtain a $CO_2$ concentration in the gas entering the reactor of 30% by volume. From a cylinder containing propane, such an amount of propane is added to the circulating gas as to obtain a propane concentration in the gas entering the reactor of 20% by volume. The propylene concentration is 27% by volume, i.e. the ratio of propane to propylene is 0.75. 4.6 kg of crude condensate per hour are obtained; the allyl acetate concentration amounts to 33.5%, that of the by-products to 0.8%, that of the water to 7.7%, corresponding to an allyl acetate space-time-yield of 350 g per liter per hour and to a propylene loss of 9.5%.

EXAMPLE 6

The reaction conditions are analogous to Example 5, but the propane amount added to the circulating gas is increased so that the propane concentration in the gas entering the reactor is 31% by volume. The propylene concentration decreases to 15%, the ratio of propane to propylene is 2.0. 4.5 kg of crude condensate per hour are obtained, the concentration of allyl acetate is 31%, that of the by-products 0.7%, that of the water 7.4%, the allyl acetate space-time-yield is 318 g per liter per hour and the propylene loss 9.7%.

What is claimed is:
1. In a process for the preparation of allyl acetate from acetic acid, propylene and oxygen in the presence of carbon dioxide wherein a vapor phase mixture of said components is reacted, in a reaction zone, over a catalyst consisting essentially of
  a. a metal or salt of a metal selected from the group consisting of palladium, platinum, ruthenium, rhodium and iridium;
  b. an alkali metal or alkaline earth metal salt; and
  c. a support for said components (a) and (b) selected from the group consisting of silicic acid, aluminum oxide and aluminum silicate, the improvement which comprises: reacting a mixture of said components in said reaction zone in which the concentration of propylene is below 50 percent by volume and propane is present in an amount of from 0.2 to 5.0 times that of propylene.

2. A process as recited in claim 1 wherein the propylene concentration in the reaction mixture is below 30 percent by volume.

3. A process as recited in claim 1 wherein said propane is present in from 0.5 to 2.0 times the amount of said propylene.

* * * * *